United States Patent
Odry et al.

(10) Patent No.: US 10,521,911 B2
(45) Date of Patent: Dec. 31, 2019

(54) IDENTIFICATION OF DEFECTS IN IMAGING SCANS

(71) Applicant: Siemens Healthcare GmbH, Erlangen (DE)

(72) Inventors: Benjamin L. Odry, West New York, NJ (US); Hasan Ertan Cetingul, Fulton, MD (US); Mariappan S. Nadar, Plainsboro, NJ (US); Puneet Sharma, Monmouth Junction, NJ (US); Shaohua Kevin Zhou, Plainsboro, NJ (US); Dorin Comaniciu, Princeton Junction, NJ (US)

(73) Assignee: Siemens Healtchare GmbH, Erlangen (DE)

( * ) Notice: Subject to any disclaimer, the term of this patent is extended or adjusted under 35 U.S.C. 154(b) by 139 days.

(21) Appl. No.: 15/831,731

(22) Filed: Dec. 5, 2017

(65) Prior Publication Data
US 2019/0172207 A1    Jun. 6, 2019

(51) Int. Cl.
| | |
|---|---|
| *A61B 6/03* | (2006.01) |
| *A61B 6/00* | (2006.01) |
| *G06T 7/11* | (2017.01) |
| *G16H 50/20* | (2018.01) |
| *G06K 9/46* | (2006.01) |
| *G16H 50/70* | (2018.01) |

(Continued)

(52) U.S. Cl.
CPC ............ *G06T 7/0016* (2013.01); *A61B 6/032* (2013.01); *A61B 6/506* (2013.01); *G06K 9/4628* (2013.01); *G06T 7/0012* (2013.01); *G06T 7/11* (2017.01); *G16H 30/40* (2018.01); *G16H 50/20* (2018.01); *G16H 50/70* (2018.01); *A61B 6/481* (2013.01); *A61B 6/501* (2013.01); *A61B 6/5247* (2013.01); *G06K 2209/05* (2013.01); *G06T 2207/10081* (2013.01); *G06T 2207/20081* (2013.01); *G06T 2207/20084* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 6,141,437 A | 10/2000 | Xu et al. | |
| 6,240,201 B1 | 5/2001 | Xu et al. | |
| 6,470,092 B1 | 10/2002 | Li et al. | |

(Continued)

FOREIGN PATENT DOCUMENTS

WO    2017106645 A1    6/2017

*Primary Examiner* — Idowu O Osifade

(57) ABSTRACT

A method of reviewing neural scans includes receiving at least one landmark corresponding to an anatomical region. A plurality of images of tissue including the anatomical region is received and a neural network configured to differentiate between healthy tissue and unhealthy tissue within the anatomical region is generated. The neural network is generated by a machine learning process configured to receive the plurality of images of tissue and generate a plurality of weighting factors configured to differentiate between healthy tissue and unhealthy tissue. At least one patient image of tissue including the anatomical region is received and a determination is made by the neural network whether the at least one patient image of tissue includes healthy or unhealthy tissue.

20 Claims, 13 Drawing Sheets

(51) Int. Cl.
*G16H 30/40* (2018.01)
*G06T 7/00* (2017.01)

(56) References Cited

U.S. PATENT DOCUMENTS 6,795,521 B2 9/2004 Hsu et al.
2014/0056842 A1* 2/2014 Sackner-Bernstein ......................
A61K 38/18
424/85.1

* cited by examiner

IDENTIFICATION OF DEFECTS IN IMAGING SCANS

FIELD

Aspects of the present disclosure relate in general to detection of abnormalities in a patient based on a scan image, and more particularly to identification of abnormalities and prioritization of scan image reviews based on abnormality detection.

BACKGROUND

Nuclear imaging, such as non-contrast computerized tomography (CT) scans, are commonly used to generate cross-sectional imaging studies during emergency and/or non-emergency medicine. Images generated during a scan (i.e., scan images) serve as a screening tool to identify defects (or abnormalities) in a patient's brain, if present. Common defects identified through non-contrast CT scans include acute hemorrhage, acute infarction, hydrocephalus, mass effect, mass lesion, and intracranial hemorrhage, among others.

In current health settings, a radiologist visually reviews each scan to identify abnormalities. Many scan images lack any visible findings but must still be reviewed, increasing patient treatment time and decreasing timeliness of critical finding identification. Existing screening workflow utilizes non-imaging information such as patient age, type and severity of incident, and manifestations of symptoms to attempt to prioritize review of scans by radiologist. Although such screening workflows can provide some filtering, existing systems can result in delayed review and identification of critical findings, lowering patient outcomes and increasing costs.

SUMMARY

In various embodiments, a method of reviewing neural scans includes receiving at least one landmark corresponding to an anatomical region and receiving a plurality of images of tissue including the anatomical region. A neural network is generated and configured to differentiate between healthy tissue and unhealthy tissue within the anatomical region. The neural network is generated by a machine learning process configured to receive the plurality of images of tissue and generate a plurality of weighting factors configured to differentiate between healthy tissue and unhealthy tissue. At least one patient image of tissue including the anatomical region is received and the neural network determines whether the at least one patient image of tissue includes healthy or unhealthy tissue.

In various embodiments, a system for reviewing neural scans includes an imaging modality configured to obtain a neural image of a patient and a processor configured to implement a neural network. The neural network is generated by receiving at least one landmark corresponding to an anatomical region, receiving a plurality of images of tissue including the anatomical region, and performing a machine learning process configured to review the plurality of images of tissue and generate a plurality of weighting factors configured to differentiate between healthy tissue and unhealthy tissue. The processor is configured to identify, via the neural network, a defect in the neural image.

In various embodiments, a non-transitory computer-readable medium encoded with computer executable instructions is also disclosed. The computer executable instructions, when executed by a computer in a system for reviewing neural scans cause the system for reviewing neural scans to execute the steps of: receiving at least one landmark corresponding to an anatomical region, receiving a plurality of images of tissue including the anatomical region, generating a neural network configured to differentiate between healthy tissue and unhealthy tissue within the anatomical region, receiving at least one patient image of tissue including the anatomical region, and determining, via the neural network, whether the at least one patient image of tissue includes healthy or unhealthy tissue. The neural network is generated by a machine learning process configured to receive the plurality of images of tissue and generate a plurality of weighting factors configured to differentiate between healthy tissue and unhealthy tissue.

BRIEF DESCRIPTION OF THE DRAWINGS

The following will be apparent from elements of the figures, which are provided for illustrative purposes and are not necessarily drawn to scale.

DETAILED DESCRIPTION

This description of the exemplary embodiments is intended to be read in connection with the accompanying drawings, which are to be considered part of the entire written description. As used herein, the term "healthy," "normal," and "defect-free" are used interchangeably to refer to an anatomical structure (such as a brain) that does not include any abnormalities, defects, or other pathologies therein. As used herein, the term "unhealthy," "abnormal," and "defect-containing" are used interchangeably to refer to an anatomical structure (such as a brain) containing at least one abnormality, defect, or other pathology.

In various embodiments, a system and method for categorizing a scan of patient's brain is disclosed. The system is configured to receive a scan image containing one or more anatomical structures, such as a brain. The scan image can be generated by an imaging device, such as a nuclear imaging system, loaded from a memory module, and/or otherwise provided to the system. The system includes a neural network configured to perform defect identification and detection. The neural network is configured to receive the scan image and generate an output with respect to the presence or absence of a defect in the scan image. The neural network can be generated by a learning network configured to receive a training data set containing a plurality of scan images.

Figure 1:
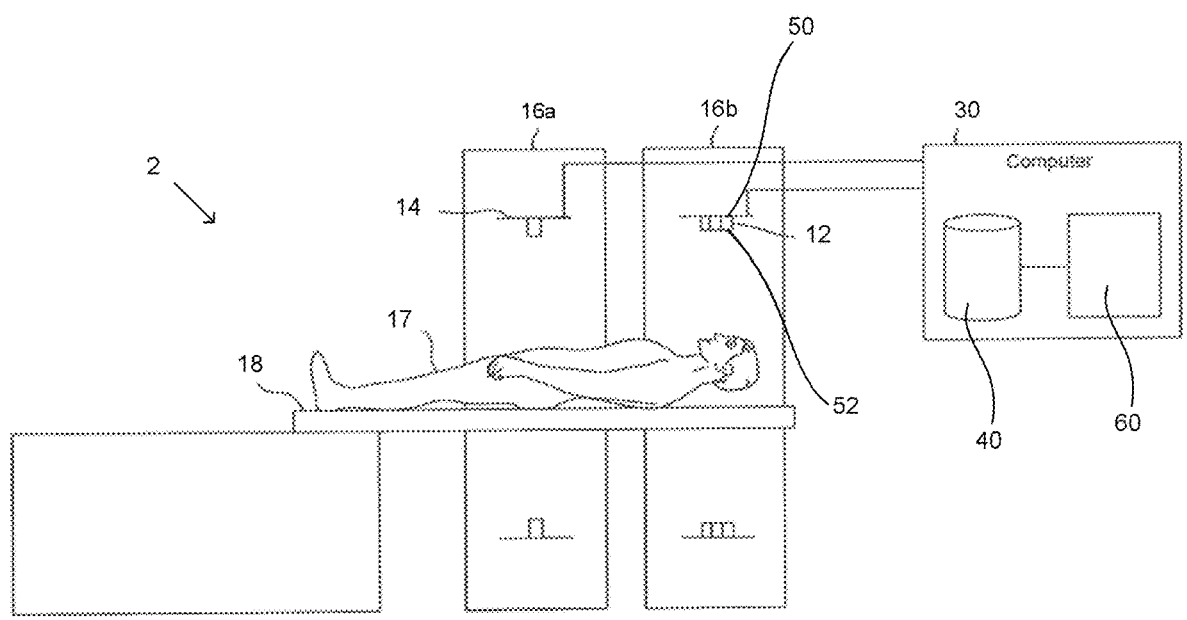
FIG. 1 illustrates a nuclear imaging system, in accordance with some embodiments.

FIG. 1 illustrates one embodiment of a nuclear imaging system 2. The nuclear imaging system 2 includes a scanner for at least a first modality 12 provided in a first gantry 16a. The first modality 12 includes a plurality of detectors 50 configured to detect an annihilation photon, gamma ray, and/or other nuclear imaging event. In various embodiments, the first modality 12 is a computerized tomography (CT) modality. A patient 17 lies on a movable patient bed 18 that may be movable between a gantry. In some embodiments, the nuclear imaging system 2 includes a scanner for a second imaging modality 14 provided in a second gantry 16b. The second imaging modality 14 can be any suitable imaging modality, such as, for example, photon emission tomography (PET) modality, single-photon emission tomography (SPECT) modality and/or any other suitable imaging modality.

Scan data from the first modality 12 is stored at one or more computer databases 40 and processed by one or more computer processors 60 of a computer system 30. The graphical depiction of computer system 30 in FIG. 1 is provided by way of illustration only, and computer system 30 may include one or more separate computing devices. The imaging data sets can be provided by the first modality 12 and/or may be provided as a separate data set, such as, for example, from a memory coupled to the computer system 30. The computer system 30 can include one or more processing electronics for processing a signal received from one of the plurality of detectors 50.

Figure 2A:
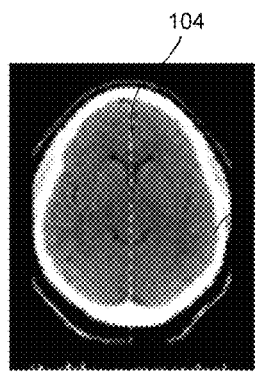
FIG. 2A illustrates a non-contrast CT scan of a healthy brain.
Figure 2B:
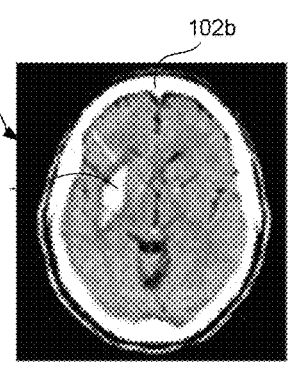
FIG. 2B illustrates a non-contrast CT scan of a brain containing an acute hemorrhage.
Figure 2C:
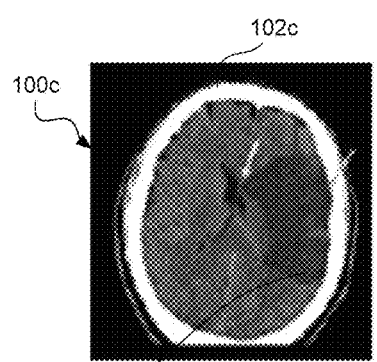
FIG. 2C illustrates a non-contrast CT scan of a brain containing a mass effect.
Figure 2D:
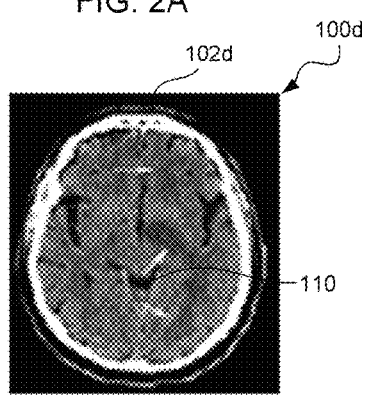
FIG. 2D illustrates a non-contrast CT scan of a brain containing an acute infarction.
Figure 2E:
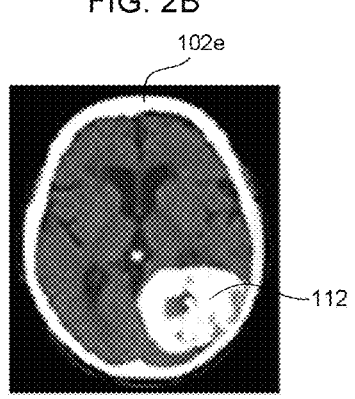
FIG. 2E illustrates a non-contrast CT scan of a brain containing a mass lesion.
Figure 2F:
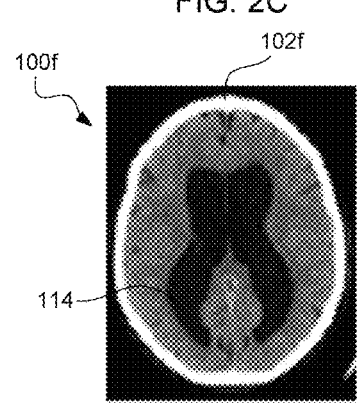
FIG. 2F illustrates a non-contrast CT scan of a brain containing a hydrocephalus.

FIG. 2A illustrates a non-contrast CT scan 100a of a defect-free brain 102a. The defect-free brain 102a is symmetric about a midsagittal plane (MSP) (or midline) 104 and contains generally uniform distribution of brain matter. FIGS. 2B-2F illustrate non-contrast CT scans 100b-100f of brains 102b-102f each having at least one defect, in accordance with some embodiments. FIG. 2B illustrates a brain 102b containing an acute hemorrhage 106. The acute hemorrhage 106 is shown as a lighter area in the CT scan 100b. FIG. 2C illustrates brain 102c having a mass effect 108, for example, caused by an edema as a result of ischemic stroke. The mass effect 108 is shown as a darker (or denser) area in the CT scan 100c. FIG. 2D illustrates a brain 102d having an acute infarction 110. The acute infarction 110 is an arterial infarction shown as a darker (or denser) area. FIG. 2E illustrates brain 102e containing a mass lesion 112. The mass lesion 112 is shown as a lighter area. FIG. 2F illustrates a brain 102f containing a hydrocephalus 114. The illustrated hydrocephalus 114 is a ventricle hydrocephalus shown as a symmetrical darker (or denser) area. Although specific defects are illustrated and discussed herein, it will be appreciated that any suitable neural defect can be identified by the system and methods disclosed herein.

Figure 3:
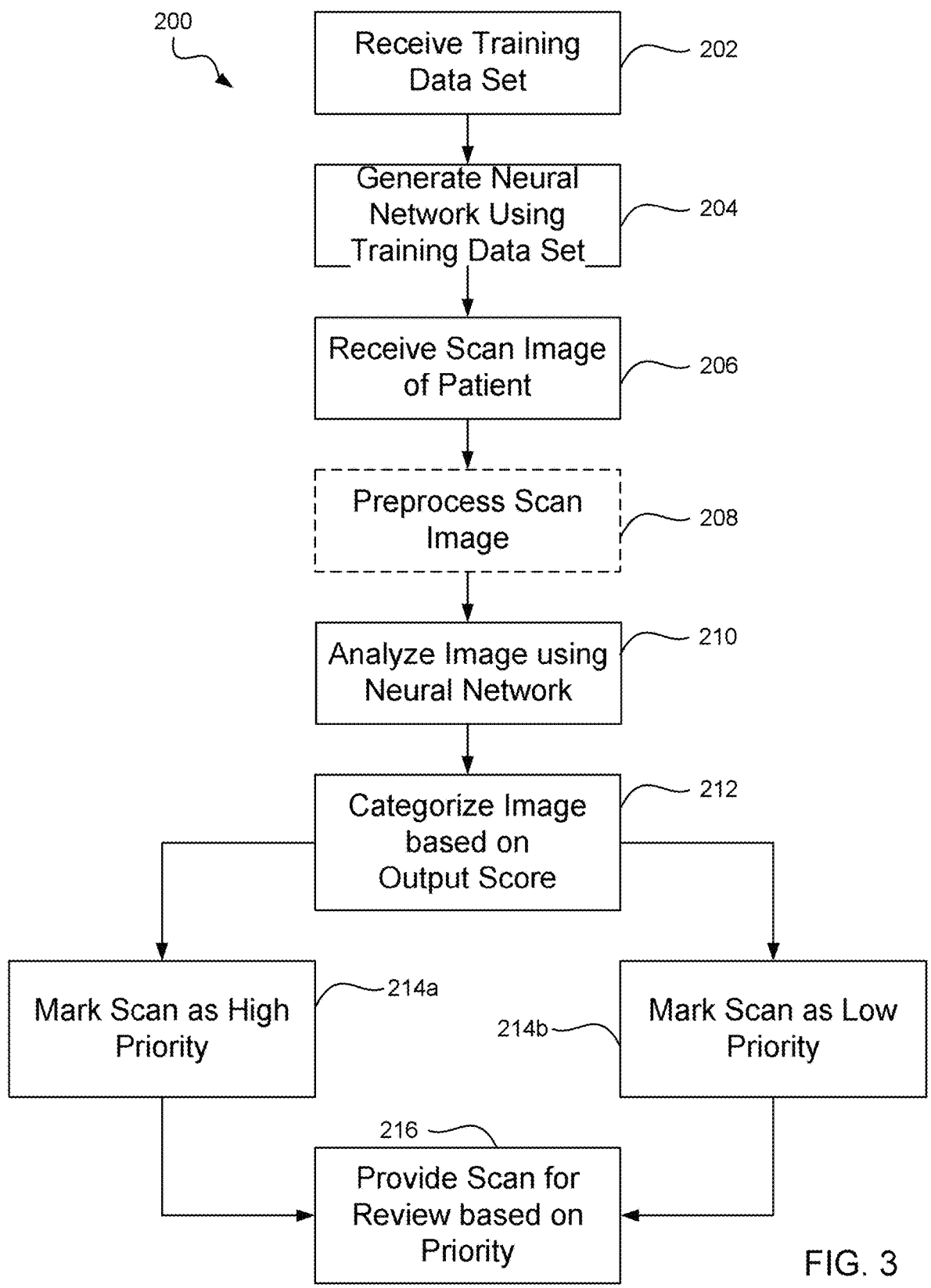
FIG. 3 is a flowchart illustrating a method of categorizing a scan using a neural network, in accordance with some embodiments.
Figure 4:
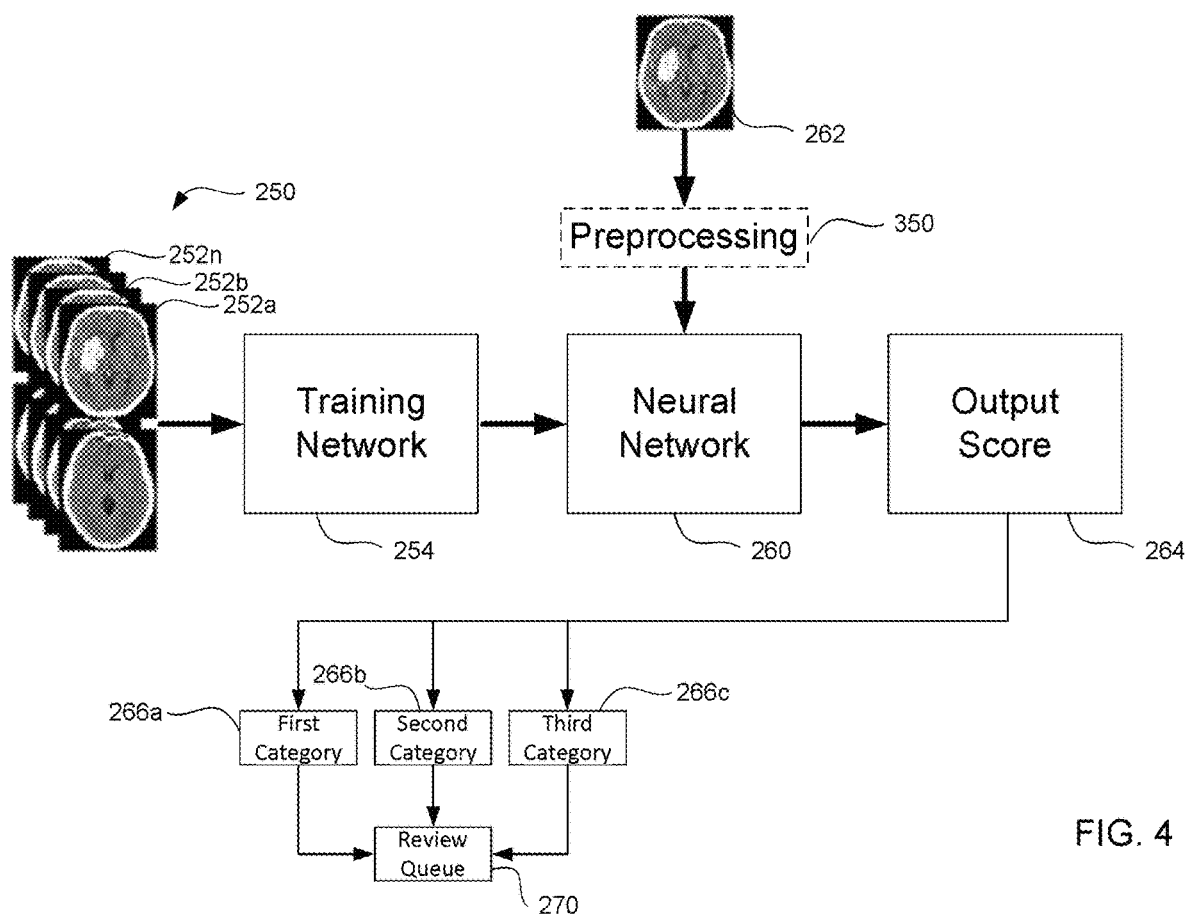
FIG. 4 illustrates the steps of the method of categorizing a scan image illustrated in FIG. 3, in accordance with some embodiments.

As shown in FIGS. 2B-2F, each of the brains 102b-102f having a defect 106-114 can be identified through non-contrast CT imaging. Identification of defects 106-114 in a timely manner is essential for providing proper and timely care to patients. FIG. 3 illustrates a method 200 of categorizing a scan image using a neural network, in accordance with some embodiments. The method 200 can be used to categorize one or more scans, such as one or more non-contrast CT scans, PET scans, SPECT scans, MRIs, etc. into a plurality of categories. For example, in some embodiments, the method 200 is configured to categorize each scan image as a high-priority scan or a low priority scan. Each scan image can be classified based on a probability of the scan containing one or more defects. In various embodiments, the method 200 can be applied to two-dimensional (2D) image slices and/or three-dimensional (3D) image volumes. FIG. 4 illustrates the various steps of the method 200 as applied to a 2D image slice 262.

At step 202, a system, such as computer system 30 illustrated in FIG. 1, receives a training data set 250. The training data set 250 contains a plurality of training images 252a-252c. The plurality of training images 252a-252c can contain healthy, unhealthy, and/or a combination of healthy and unhealthy anatomical structure, such as healthy and/or unhealthy neurological scan images. Each of the training images 252a-252c can include associated data identifying information related to the training image 252a-252c, such as the presence and/or absence of a defect, the type of defect, a location of the defect, and/or any other suitable information. In some embodiments, the system 30 receives a plurality of training data sets 250 each containing a plurality of training images 252a-252c with associated data. For example, the system 30 can receive a first training data set containing only healthy brains, a second training data set containing only unhealthy brains having a first defect (such as an acute hemorrhage), a third training data set containing only unhealthy brains having a second defect, etc. The training data set(s) 250 can be received from a single source and/or can be received from multiple sources.

At step 204, the system 30 generates a neural network 260 using the training data set 250. The neural network 260 is generated by providing each of the training images 252a-252c in the training data set 250 to a learning network 254, such as an image-to-image learning network, a deep reinforcement learning network, a residual network, a densely connected convolution network, and/or any other suitable learning network. The learning network 254 reviews each of the training images 252a-252c and attempts to identify one or more parameters, such as the presence or absence of a defect, type of defect, location of a defect, etc. The learning network 254 can utilize any suitable learning algorithm, such as an optimization and/or statistical estimation algorithm, as just one example. In some embodiments, the learning network 254 is configured to identify one or more landmarks. For example, in various embodiments, the generated neural network 260 is configured to detect one or more hemispheres, lobes, an occipital bone, orbital bones, crista galli, superior sagittal sinuses, falx cerebri, bregma (intersection of coronal and sagittal sutures) and/or any other suitable landmark. The generated neural network 260 can be configured to identify the locations of landmarks and/or use the landmarks to estimate other elements of the scan image, such as a mid-sagittal plane.

In some embodiments, the learning network 254 is a supervised learning network. A supervised learning networks receives the training data set 250 and attempts to identify a neural network mapping (e.g., a neural network topography) implied by the training data set 250 and that best maps a set of inputs (training images 252a-252c) to their correct output. For example, a supervised learning network provided with a training data set 250 containing healthy brains and unhealthy brains generates a neural network 260 that best maps health and unhealthy brains to selected categories. A cost function is related to a mismatch between the selected mapping and the training data set 250. The cost function can include any suitable cost function, such as a mean-squared error function or categorical cross entropy loss function. In some embodiments, the learning network 254 uses a backpropagation algorithm to calculate an error contribution of each neuron (e.g., node) in the neural network 260 during training. The cost function is configured to identify the best neural network topography based on the training data set 250.

At step 206, the system 30 receives a scan image 262, such as a non-contrast CT scan image. In some embodiments, the scan image 262 is generated by a nuclear imaging system, such as the nuclear imaging system 2 illustrated in FIG. 1. In other embodiments, the scan image 262 is received from a networked system and/or storage device. The scan image 262 can contain one or more defects (i.e., the scan image 262 is of an unhealthy brain) or contain no defects (i.e., the scan image 262 is of a healthy brain).

At optional step 208, the scan image 262 is pre-processed to prepare the scan image 262 for review by the neural network 260. For example, in some embodiments, the system 30 is configured to identify one or more landmarks in the scan image 262 and estimate a midsagittal plane of the brain. In some embodiments, the scan image 262 is rotated to orient the estimated midsagittal plane in a predetermined position, such as in the center of a modified scan image. Such preprocessing can be used to increase accuracy of the neural network 260 and decrease review time. Although step 208 is shown as a distinct pre-processing step, it will be appreciated that preprocessing of the scan image 262 can occur as part of and/or simultaneously with review of the scan image 262 by the neural network 260.

At step 210, the scan image 262 is analyzed by the neural network 260 to generate an output score 264 for the scan image 262. The output score 264 is indicative of one or more characterizations of the scan image 262 by the neural network 260. The output score 264 can include a probability that the scan image 262 contains a defect, a probability related to the presence or absence of a specific defect, the type of defect, the location of a defect, a confidence level in the determination of the presence and/or absence of a defect, and/or any other suitable value. The output score 264 can include a binary indication regarding one or more parameters and/or can include a value between predetermined threshold values, such as a probability between 0 and 1. It will be appreciated that the output score 264 can include any suitable output indicating the presence, absence, and/or likelihood of one or more parameters identified by the neural network 260.

At step 212, the scan image 262 is categorized based on the output score 264. For example, in some embodiments, the output score 264 is compared to a threshold value to determine whether the scan image 262 has a high probability or a low probability of containing a defect. The threshold value can be a predetermined value and/or a value generated by the neural network 260. The threshold value can be related to a confidence value of the determination of the absence or presence of a defect in the scan image 262, a minimum probability required for identifying a scan image 262 as likely containing a defect, and/or any other value related to the presence and/or absence of a defect. In some embodiments, the scan image 262 is categorized based on multiple features and/or scores into one or more of a plurality of categories 266a-266c. For example, a scan image 262 can be categorized into one of a plurality of categories 266a-266c corresponding to specific defects (or the absence thereof). Although embodiments are discussed herein include specific categorizations, it will be appreciated that the output score 264 can be used to categorize the scan image 262 into any suitable category (or categories).

In some embodiments, if a scan image 262 is categorized as one or more categories in a first set, such as first category 266a and/or second category 266b, the method 200 proceeds to step 214a and the scan image 262 is identified as a high-priority scan. For example, in various embodiments, if the scan image 262 is categorized as a high-priority scan, categorized as having an output score above a predetermined minimum probability threshold, categorized as likely containing a defect, and/or any other suitable categorization, the scan image 262 is identified (or marked) as being a high-priority scan. In some embodiments, if the scan image 262 is categorized in one or more categories in a second set, such as third category 266c, the method 200c proceeds to step 214b and the scan image is identified/marked as a low-priority scan. For example, in various embodiments, if the scan image 262 is categorized as a low-priority scan, categorized as having an output score below a predetermined minimum probability threshold, categorized as not likely containing a defect, and/or any other suitable categorization, the scan image 262 is identified (or marked) as being a low-priority scan.

At step 216, the scan image 262 is placed in a review queue 270. The scan image 262 can be placed in a queue based on the categorization generated by the neural network 260 and/or a marking/identification of the scan image 262. For example, in some embodiments, if the scan image 262 is categorized as a high-priority scan at step 214a, the scan image 262 is placed earlier or at the beginning of the review queue 270. Similarly, if the scan image 262 is categorized has a low-priority scan, the scan image 262 is placed at the end of or later in the review queue 270. In some embodiments, scan images 262 that are marked as high-priority are routed to a first review queue 270 for review by a first set of reviewers (such as neuro-radiologist) and scan images 262 that are marked as low-priority are routed to a second review queue 270 for review by a second set of reviewers (such as general radiologist). In some embodiments, scan images 262 having a probability score below a predetermined threshold are not reviewed. The reviewer can confirm the presence of a defect in the scan image 262 and provide treatment and/or guidance to the patient or treatment team based on the review.

Figure 5:
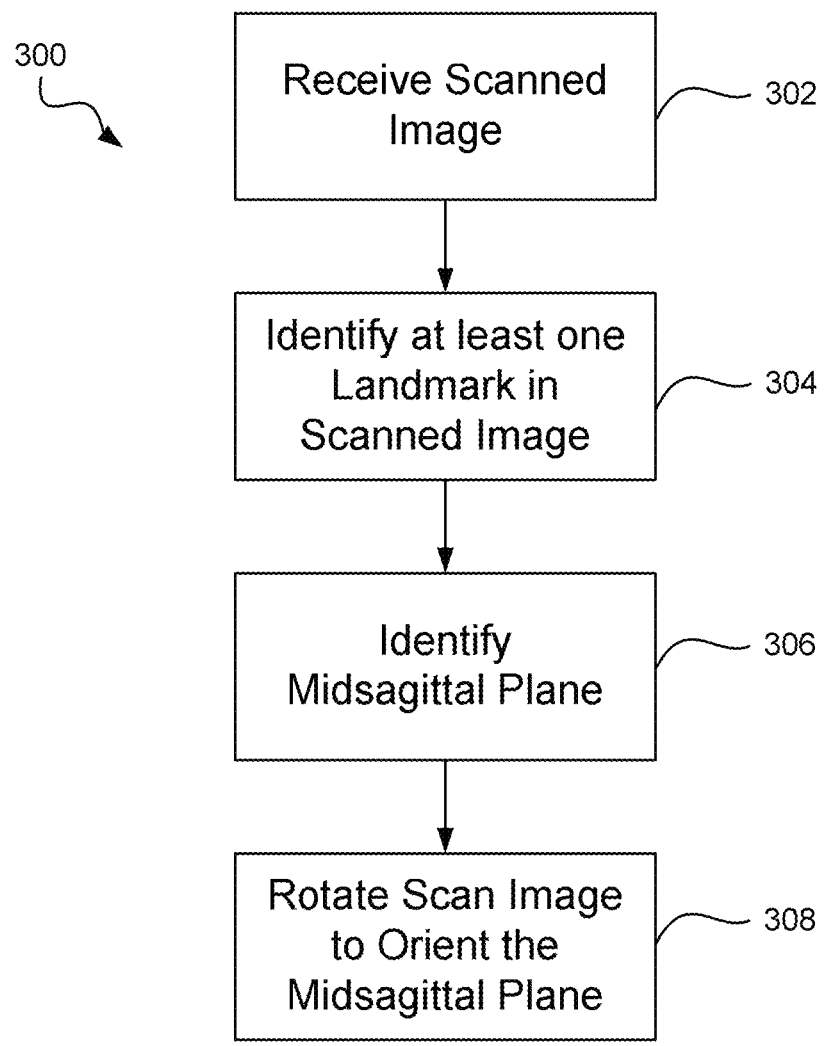
FIG. 5 is a flowchart illustrating a method of data preparation for processing by the neural network, in accordance with some embodiments.
Figure 6:
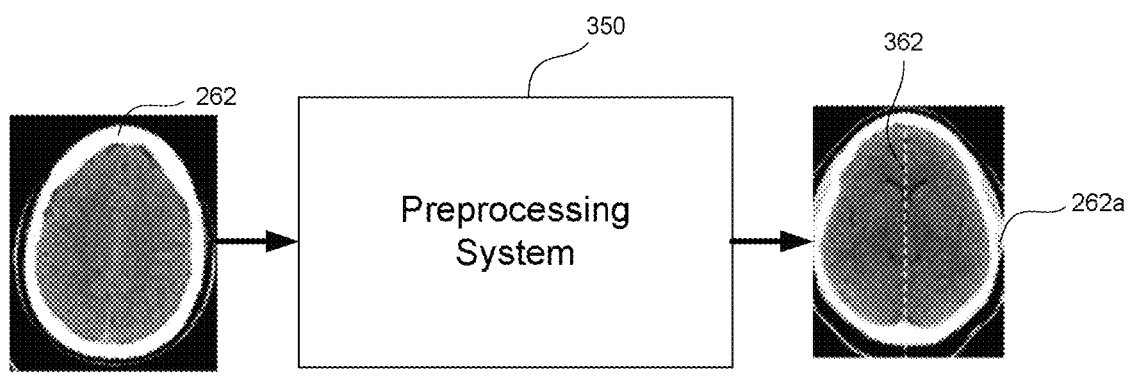
FIG. 6 illustrates the steps of the method of data preparation illustrated in FIG. 5, in accordance with some embodiments.

In some embodiments, the neural network 260 implements a preprocessing step, such as step 208 discussed above. FIG. 5 illustrates a method 300 of data preparation for preprocessing by the neural network, in accordance with some embodiments. FIG. 6 illustrates the various steps of the method 300 and is discussed in conjunction with FIG. 5. At step 302, a scan image 262 is received by a preprocessing system 350. In some embodiments, the preprocessing system 350 is the same system executing a method of categorizing a scan using a neural network (such as method 200 discussed above). In other embodiments, the preprocessing system 350 is separate from the categorizing system and in signal communication therewith. The scan image 262 can be received from any suitable source. For example, in various embodiments, the scan image can be an image obtained from a training data set 250, obtained from an imaging device 2, obtained from a memory unit, and/or obtained from any other suitable source.

At step 304, one or more landmarks are identified in the scan image 262. The one or more landmarks correspond to anatomical structures that are present in similar (or identical) locations in healthy brains. For example, in various embodiments, landmarks can include one or more of cristal galli, superior sagittal sinuses, falx cerebri, an occipital bone (or portion thereof), and/or any other suitable anatomical structure. Priority can be given to one or more landmarks and/or all identified landmarks can be ranked equally.

At step 306, a midsagittal plane 362 is identified. The midsagittal plane 362 can be identified based on the relative and/or absolute positions of one or more of the landmarks. For example, in some embodiments, one or more of the landmarks correspond to a position with respect to the midsagittal plane, such as left-of, right-of, and/or aligned with the midsagittal plane. Identification of a predetermined number of landmarks having known orientations and/or positions with respect to the midsagittal plane allows the preprocessing system 350 to estimate the location of the midsagittal plane 362 of the scan image 262. It will be appreciated that any suitable model(s) can be used to identify and/or position a midsagittal plane 362.

At step 308, the scan image 262 is rotated to orient the scan image along the estimated (or known) midsagittal plane 362 in a predetermined position, such as aligned with a vertical and/or horizontal center of the scan image 262, to generate a uniform image 262a. Orientation of the uniform image 262a ensures that each scan image 262 reviewed by the neural network 260 is similarly presented. In some embodiments, orientation of the uniform image 262a can also include resampling and/or other modification of the scan image 262. Providing similarly sized and/or oriented images increases accuracy of the neural network 260 and decreases review time.

Figure 7:
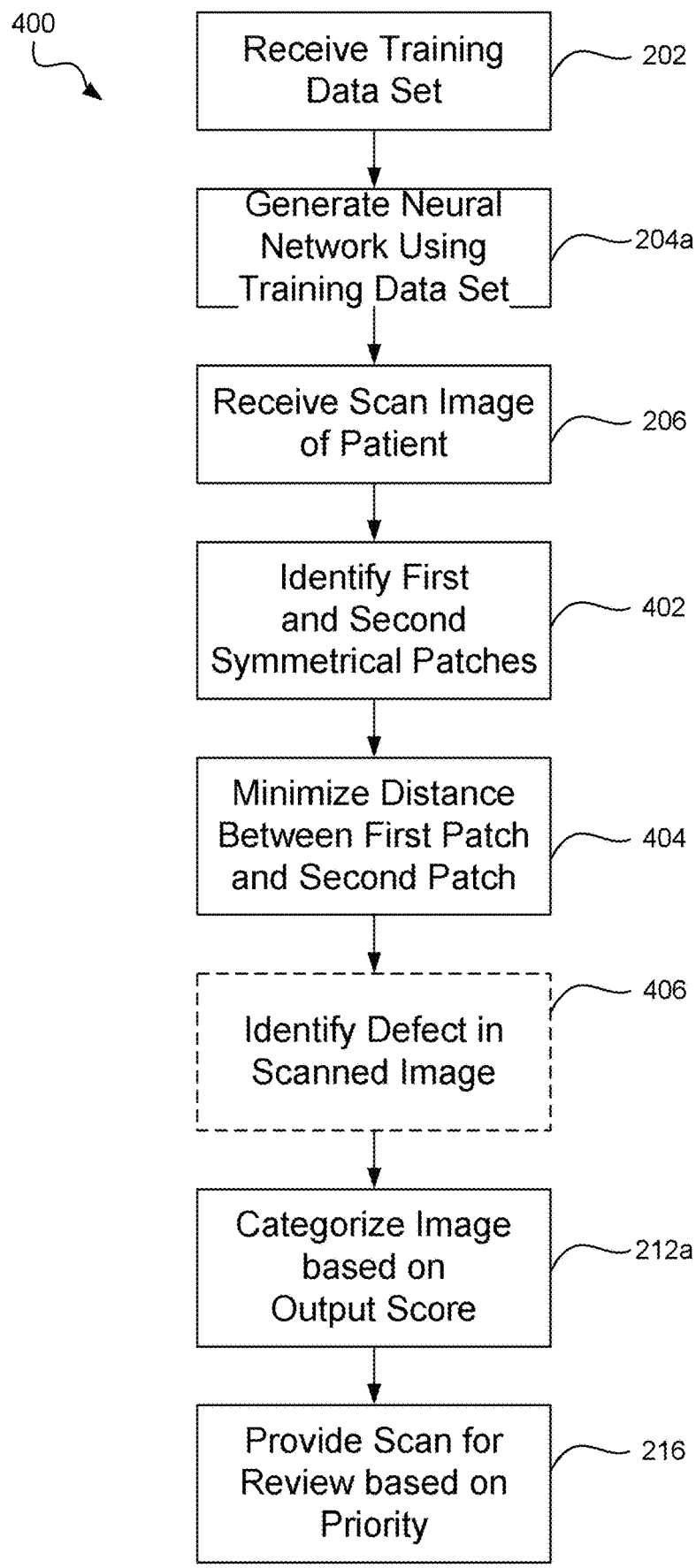
FIG. 7 is a flowchart illustrating illustrates a method of categorizing a scan image based using symmetrical patches, in accordance with some embodiments.
Figure 8:
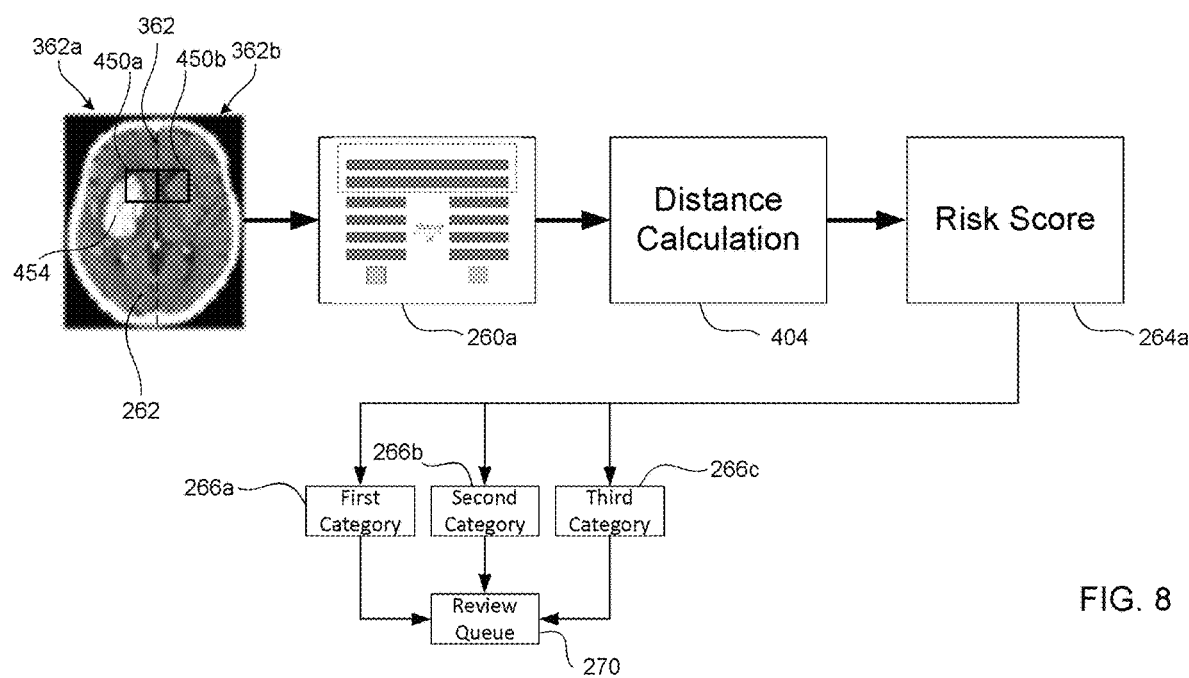
FIG. 8 illustrates the method of categorizing a scan image of FIG. 7 using a Siamese network, in accordance with some embodiments.
Figure 9:
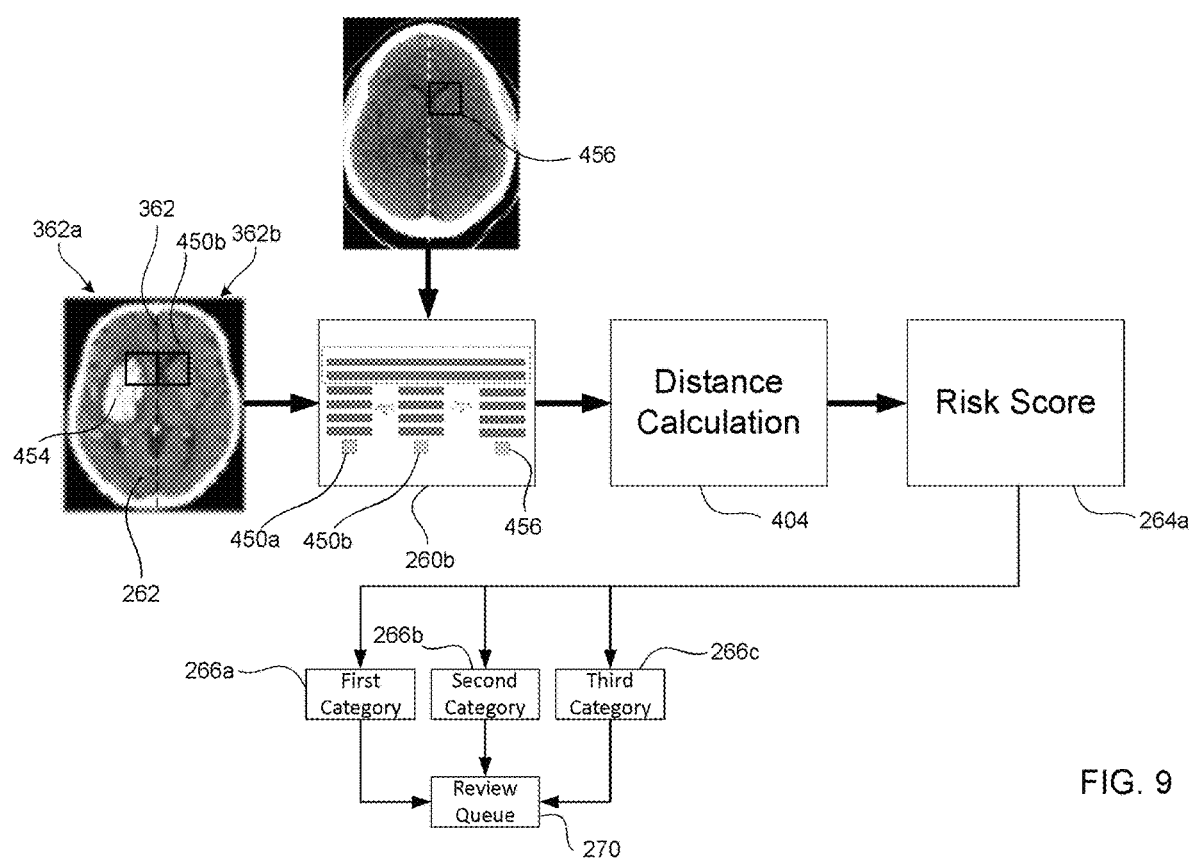
FIG. 9 illustrates the method of categorizing a scan image of FIG. 7 using a triplet network, in accordance with some embodiments.

FIG. 7 illustrates a method 400 of categorizing a scan image 262 using a plurality of symmetrical patches, in accordance with some embodiments. The method 400 is similar to the method 200 discussed above in conjunction with FIGS. 3-4, and similar description is not repeated herein. FIGS. 8-9 illustrate the various steps of the method 400 and are discussed in conjunction with FIG. 7. At step 204a, a neural network 260 is generated using a training data set 250 containing a plurality of training images 252a-252c each containing a plurality of symmetrically positioned patches.

At step 402, the system 30 identifies a first patch 450a centered at a point on a first side 362a of a mid-sagittal plane 362 of a scan image 262 and a second patch 450b centered at a point on a second side 362a of the mid-sagittal plane 362. The first patch 450a and the second patch 450b are symmetrically located about the mid-sagittal plane 362.

At step 404, a distance between the first patch 450a and the second patch 450b is minimized. As used herein, the term "distance" is used to denote the differences or dissimilarities between a first patch and a second patch. In a healthy brain, symmetrically located patches 450a, 450b are generally similar and have a small (or low) distance therebetween. However, in an unhealthy brain, the distance between symmetrically located patches 450a, 450b including a non-symmetrical defect (e.g., acute hemorrhage, acute infarct, mass lesion, mass effect, etc.) will be greater.

In some embodiments, a distance between the first patch 450a and the second patch 450b is determined using a Siamese network 260a configured to receive pairs of symmetrically located patches 450a, 450b as inputs, as shown in FIG. 8. The Siamese network 260a includes at least two branches that share weighting factors and that are driven by a hinge-based loss term and L2-norm regularization. Each of the branches classifies a received patch 450a, 450b as healthy or unhealthy. The determination of each branch is compared to identify non-symmetries in the patches 450a, 450b, for example, based on the difference between the classification of the patches 450a, 450b, difference in output scores 264 for each of the patches, and/or any other variation identified by the Siamese network 260a.

In some embodiments, the Siamese network 260a is configured to receive a plurality of multi-scale patches 450a, 450b for defect detection. The Siamese network 260a can include a plurality of pairs of network paths for processing a pairs of patches 450a, 450b. Each of the plurality of pairs of network paths include identical weighting factors for each path in the pair. In some embodiments, each pair of network paths receives a pair of rescaled symmetrical patches 450a, 450b. Each pair of rescaled symmetrical patches 450a, 450b is centered at symmetrical points with respect to a midsagittal line 362 and can have a different applied scaling factor. The comparison and determination of the presence or absence of a defect is conducted based on a review of each of the plurality of pairs of network paths.

In some embodiments, the distance between the first patch 450a and the second patch 450b is calculated using a triplet network 260b, as shown in FIG. 9. The triplet network 260b is configured to receive pairs of symmetrical patches 450a, 450b at each set of network paths. Each of the sets of network paths also receives a third input 456. In some embodiment, the third input 456 includes a reference patch. For example, in some embodiments, the reference patch corresponds to the position of one of the first patch 450a or the second patch 450b but taken from a known-healthy image. The third input 456 causes the learning network 250 to generate a network based on description of patch differences as opposed to descriptions of the patches 450a, 450b, 456 themselves.

At optional step 406, a defect 454 (or abnormality) in the scan image 250 can be identified and highlighted based on the descriptions provided by the neural network 260a, 260b, such as the distance determination or other descriptors. In some embodiments, multiple loss functions are applied by the neural network 260a, 260b. Each of the loss functions can be applied to further differentiate patches 450a, 450b to identify specific defects within low and/or non-symmetrical patches 450a, 450b.

At step 212a, the pair of patches 450a, 450b is classified into a class based on the distance between the patches 450a, 450b. For example, in some embodiments, the patches 450a, 450b can be classified into a class of "healthy" or "unhealthy." In other embodiments, each of the sets of patches 450a, 450b can be classified into classes of "similar" or "dissimilar" based on the distance calculation. Although specific embodiments and classes are discussed herein, it will be appreciated that any number of classes can be used by the neural network 260. For example, in embodiments including optional step 406, the classification of the patches 450a, 450b can include classification of an identified defect in the scan image.

In some embodiments, the classification includes a risk (or output) score for each finding generated by the neural network 260a, 260b. For example, in some embodiments, a Siamese network 260a or triplet network 260b is configured to detect a plurality of defects. A risk score is generated for the probability of a scan image 262 containing each of the plurality of defects. The risk score can include a number between, for example, 0 and 1 corresponding to the likely presence of a specific defect within the scan image. In some embodiments, the risk score can be a binary output indicating distance (or likelihood of a defect) above or below a predetermined threshold.

In some embodiments, the classification includes a composite score generated by combining the probabilities of each category into a single composite risk score. For example, in some embodiments, neural network 260 is configured to calculate a probability for each of a plurality of defects based on the distance between the symmetrically positioned patches 450a, 450b. The individual probabilities can be combined into a single probability (for example, a weighted probability) that the scan image 262 contains at least one defect. The composite score can be used to classify a scan image 262 for review.

Figure 10:
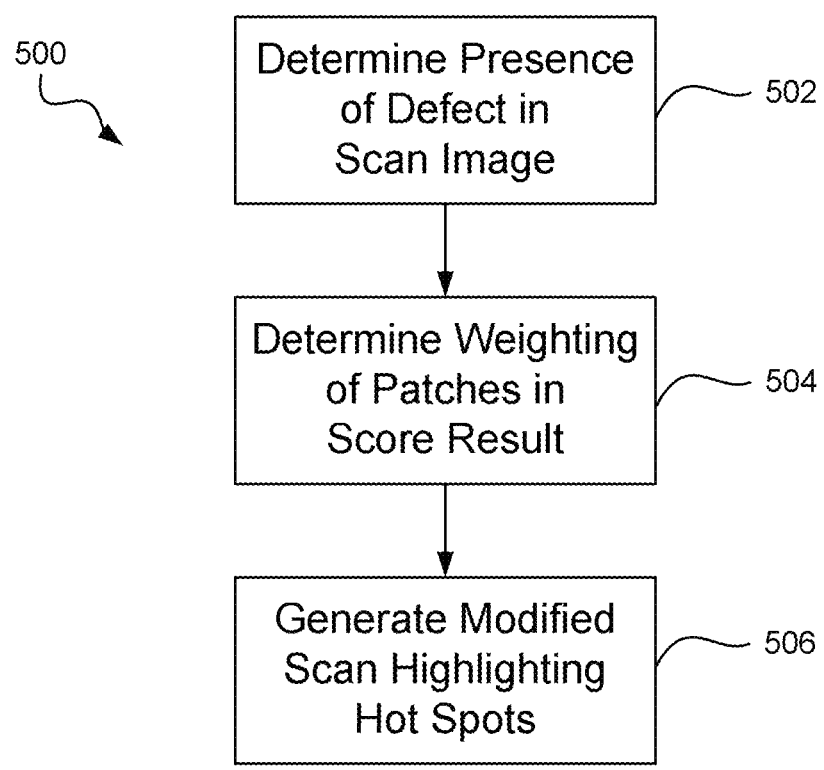
FIG. 10 is a flowchart illustrating a method of localization for identifying and displaying regions of interest, in accordance with some embodiments.
Figure 11:
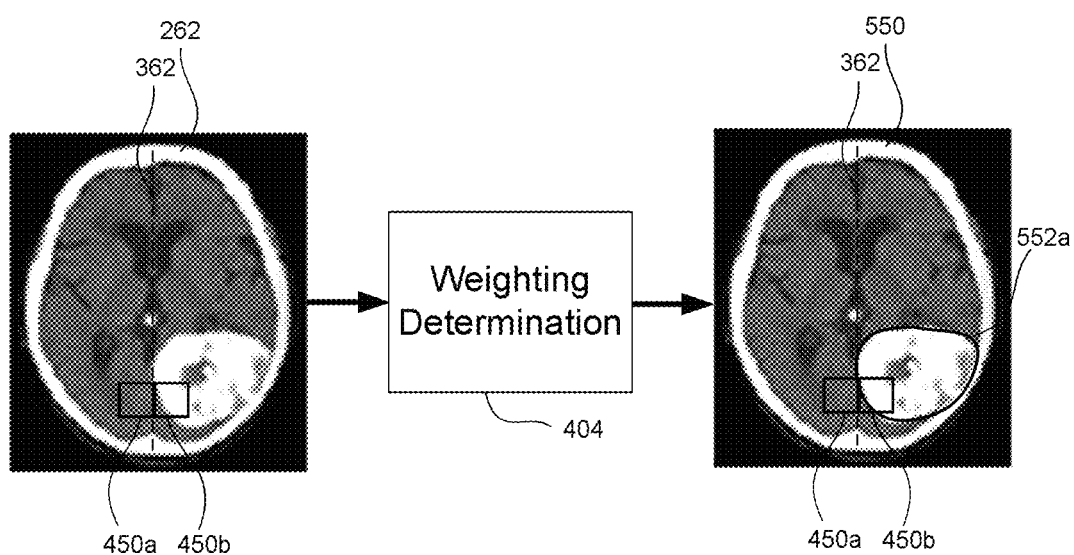
FIG. 11 illustrates the method of localization of FIG. 10, in accordance with some embodiments.

FIG. 10 illustrates a method 500 of localization for identifying defects, in accordance with some embodiments. FIG. 11 illustrates the various steps of the method 500, in accordance with some embodiments. At step 502, the neural network 260 determines the presence of a defect in a scan image 262, for example, according to one or more of the methods previously discussed. In some embodiments, the neural network 260 is a Siamese 260a or triplet network 260b configured to receive symmetrical patches 450a, 450b as discussed above, although it will be appreciated that the neural network 260 can identify defects according to any of the methods discussed herein.

At step 504, the neural network 260 determines which portions (or patches) of the scan image 262 most impacted the determination of the presence of a defect, i.e., hot spots within the scan image 262. For example, in some embodiments, the neural network 260 utilizes a plurality of patches 450a, 450b to identify areas that include one or more known defects. The neural network 260 can identify the areas of highest deviation from healthy and/or symmetrical comparison patches. The patches having the highest deviation can be identified during and/or after the determination that a defect is likely present in the scan image 262.

At step 506, the system 30 generates a modified scan image 550 highlighting the hot-spots identified in step 504. The modified scan image 550 includes one or more highlighted areas 552a corresponding to the portions of the scan image 262 having the greatest impact on the neural network 260 determination, for example, patches having the greatest deviation from healthy and/or symmetrical comparison patches. In some embodiments, the identified areas correspond to a probable location of the identified defect(s) within the scan image 262. The highlighted area(s) 552a allows for quick confirmation by a reviewer.

Figure 12:
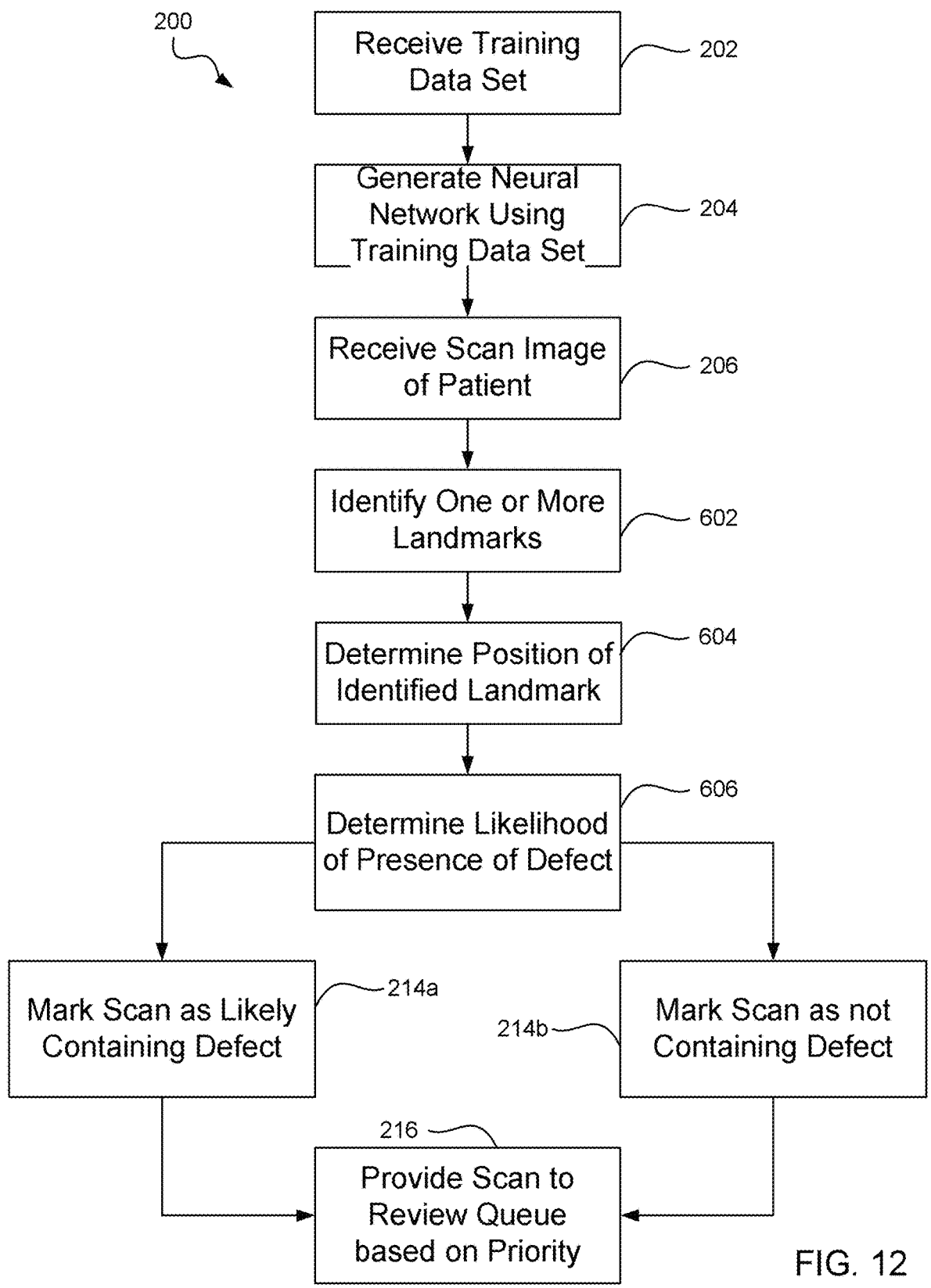
FIG. 12 is a flowchart illustrating a method of categorizing a scan image using landmark deviation, in accordance with some embodiments.

FIG. 12 illustrates a method 600 of identifying a defect in a scan image 262 using neural network 260 configured to identify landmark deviation, in accordance with some embodiments. The method 600 is similar to the method 200 discussed above, and similar description is not repeated herein. At step 602, one or more landmarks are identified in the scan image 262. The one or more landmarks correspond to anatomical structures that are present in similar (or identical) locations in healthy brains. For example, in various embodiments, landmarks can include one or more of a cristal galli, superior sagittal sinuses, falx cerebri, an occipital bone (or portion thereof), and/or any other suitable anatomical structure. In various embodiments, the neural network 260 includes a deep image-to-image network and/or a multi-scale deep reinforcement learning network to identify reference anatomical landmarks, although it will be appreciated that any suitable neural network 260 can be used. The neural network 260 can include a fully convolutional implementation using full-size images and/or volumes (as compared to 2D/3D patches) for time-efficiency. Feature concatenation and deep supervision can be applied to increase accuracy of landmark identification. In some embodiments, the neural network 260 is trained to follow an optimal navigation path to one or more landmarks within the scan image 262. The neural network 260 can be trained to identify one or more landmarks using a large number of images with annotations (i.e., indications) of the landmarks together with labels (e.g., indication of healthy or unhealthy brain) to differentiate defects and/or other factors. In some embodiments, the annotations provide a discriminative mechanism during learning and training of the neural network 260.

At step 604, the position of at least a first landmark is determined. The position of the first landmark can be indicative of a healthy or unhealthy brain. When a defect is present, the first landmark can be displaced from an anatomically correct position in one or more directions. In some embodiments, the position and/or projection of a first landmark is measured with respect to the estimated and/or determined position of the first landmark in a healthy brain (as established during neural network 260 training). In other embodiments, the position and/or projection of a first landmark is determined with respect to one or more additional landmarks. Although steps 602 and 604 are shown as distinct steps, it will be appreciated that the steps can be combined into a single determination by the neural network 260.

At step 606, the neural network 260 determines the likelihood of a defect being present in the scan image 262 based on the position of one or more identified landmarks. For example, in some embodiments, the neural network 260 utilizes deep generative approaches (such as variational autoencoders (VAE), generative adversarial networks (GANs), etc.), although it will be appreciated that the neural network 260 can use any suitable criteria for identifying defects based on a relative position of landmarks. For example, in embodiments including a VAE, shape variability in the data is encoded by projecting the data on a manifold, where abnormal scans are anticipated to be positioned away from the normal appearing ones. As another example, in embodiments including a GAN, the abnormal scans are expected to have a lower likelihood (e.g., a lower match) when provided to a discriminative network when the GAN is trained using normal scans. Although specific embodiments are discussed herein, it will be appreciated that the neural network 260 can utilize any suitable approach for identifying defects.

At step 216, the neural network 260 provides the scan image 262 to the review queue 270 based on the priority determination in step 606 for review by a radiologist (or other reviewer). In some embodiments, expert knowledge (e.g., processed diagnostic reports including semantic information with respect to anatomy) regarding how landmarks are affected by the most common and critical defects can be used to identify the type of abnormality and the severity to prioritize review of the scan image 262, although it will be appreciated that any suitable prioritization measures can be used. Knowing the location of landmarks with respect to others can help determine whether displacements occur for certain landmarks, indicating abnormality. Depending on the pathology, the surrounding tissues, or bone of the landmarks can also be affected (i.e edema after hemorrhage causing the brain tissue to show darker in the scan image), therefore also introducing additional features to characterize the abnormality.

Figure 13:
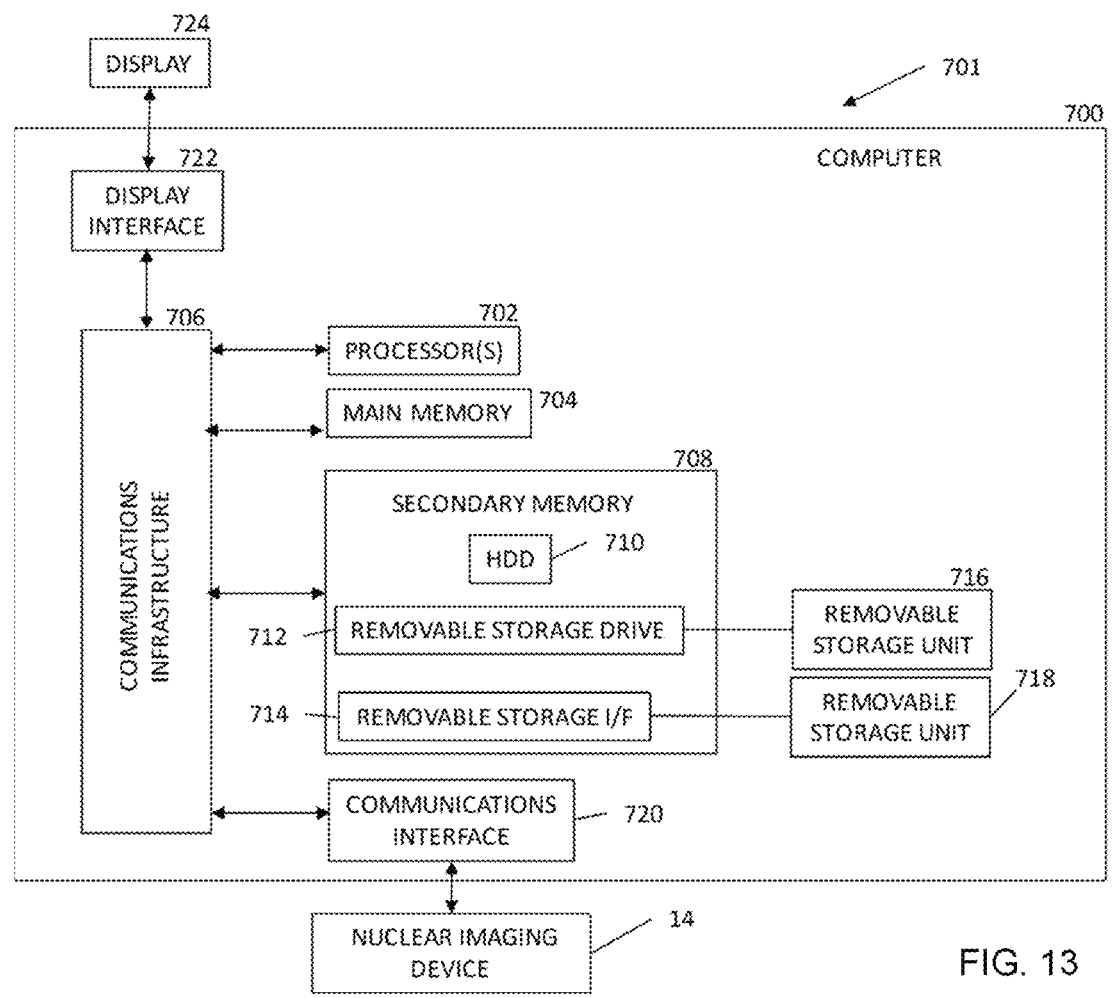
FIG. 13 is a block diagram of a computer system, in accordance with some embodiments.

FIG. 13 is a block diagram of a system 700 including the nuclear imaging detector 2 and a computer system 700. The computer system 30 can be used in some embodiments, e.g., for implementing the system 30 controlling the nuclear imaging detector 2. Computer system 500 may include one or more processors 502. Each processor 502 is connected to a communication infrastructure 506 (e.g., a communications bus, cross-over bar, or network). The processor 500 can be implemented as a central processing unit, an embedded processor or microcontroller, or an application-specific integrated circuit (ASIC). Computer system 500 may include a display interface 522 that forwards graphics, text, and other data from the communication infrastructure 506 (or from a frame buffer, not shown) for display on the display unit 524 to a user.

Computer system 500 may also include a main memory 504, such as a random access memory (RAM), and a secondary memory 508. The main memory 504 and/or the secondary memory 508 comprise a dynamic random access memory (DRAM). The secondary memory 508 may include, for example, a hard disk drive (HDD) 910 and/or removable storage drive 512, which may represent a solid state memory, an optical disk drive, a flash drive, a magnetic tape drive, or the like. The removable storage drive 512 reads from and/or writes to a removable storage unit 516. Removable storage unit 516 may be an optical disk, magnetic disk, floppy disk, magnetic tape, or the like. The removable storage unit 516 may include a computer readable storage medium having tangibly stored therein (or embodied thereon) data and/or computer software instructions, e.g., for causing the processor(s) to perform various operations.

In alternative embodiments, secondary memory 508 may include other devices for allowing computer programs or other instructions to be loaded into computer system 500. Secondary memory 508 may include a removable storage unit 518 and a corresponding removable storage interface 514, which may be similar to removable storage drive 512, with its own removable storage unit 516. Examples of such removable storage units include, but are not limited to, universal serial bus (USB) or flash drives, which allow software and data to be transferred from the removable storage unit 516, 518 to computer system 500.

Computer system 500 may also include a communications interface (e.g., networking interface) 520. Communications interface 520 allows instructions and data to be transferred between computer system 500 and nuclear imaging detector 2. Communications interface 520 also provides communications with other external devices. Examples of communications interface 520 may include a modem, Ethernet interface, wireless network interface (e.g., radio frequency, IEEE 802.11 interface, Bluetooth interface, or the like), a Personal Computer Memory Card International Association (PCMCIA) slot and card, or the like. Instructions and data transferred via communications interface 520 may be in the form of signals, which may be electronic, electromagnetic, optical, or the like that are capable of being received by communications interface 520. These signals may be provided to communications interface 520 via a communications path (e.g., channel), which may be implemented using wire, cable, fiber optics, a telephone line, a cellular link, a radio frequency (RF) link and other communication channels.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific connections, circuits, and algorithms for implementing the methods disclosed herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method of reviewing neural scans, comprising:
   receiving at least one landmark corresponding to an anatomical region;
   receiving a plurality of images of tissue including the anatomical region;
   generating a neural network configured to differentiate between healthy tissue and unhealthy tissue within the anatomical region, wherein the neural network is generated by a machine learning process configured to receive the plurality of images of tissue and generate a plurality of weighting factors configured to differentiate between healthy tissue and unhealthy tissue;
   receiving at least one patient image of tissue including the anatomical region; and
   determining, via the neural network, whether the at least one patient image of tissue includes healthy or unhealthy tissue.

2. The method of claim 1, wherein the neural network includes a first set and a second set of identical nodes, wherein the anatomical region comprises a symmetrical anatomical region, and wherein the at least one patient image includes a first patch corresponding to a first side of the symmetrical anatomical region and a second patch corresponding to a second side of the symmetrical anatomical region.

3. The method of claim 2, wherein the first patch is provided to the first set of identical nodes and the second patch is provided to the second set of identical nodes.

4. The method of claim 2, wherein the neural network comprises a third set of identical nodes, wherein the third set of identical nodes is configured to receive a reference patch.

5. The method of claim 1, wherein the network includes a plurality of skip connections configured to minimize overfitting.

6. The method of claim 1, comprising generating, via the neural network, impact maps configured to identify an influence of one or more voxels in the determination.

7. The method of claim 1, wherein the plurality of images and the at least one patient image are contrast computed tomography images.

8. The method of claim 1, comprising:
receiving a plurality of patient images;
determining, via the neural network, a severity of unhealthy tissue in each of the plurality of patient images;
ranking, by the neural network, each of the plurality of patient images according to the determined severity of unhealthy tissue; and
providing each of the plurality of patient images in rank order for further review.

9. The method of claim 1, wherein the neural network is configured to identify at least one of a hemorrhage, an acute infarct, hydrocephalus, a mass effect, and/or a mass lesion.

10. The method of claim 1, wherein the neural network is configured to identify unhealthy tissue based on a change in a position of at least one landmark.

11. The method of claim 1, wherein the neural network is a supervised learning network.

12. A system for reviewing neural scans, comprising:
an imaging modality configured to obtain a neural image of a patient; and
a processor configured to implement a neural network, wherein the neural network is generated by:
receiving at least one landmark corresponding to an anatomical region;
receiving a plurality of images of tissue including the anatomical region; and
performing a machine learning process configured to review the plurality of images of tissue and generate a plurality of weighting factors configured to differentiate between healthy tissue and unhealthy tissue;
wherein the processor is configured to identify, via the neural network, a defect in the neural image.

13. The system of claim 12, wherein the neural network includes a first set and a second set of identical nodes, wherein the neural scan includes a first patch corresponding to a first side of a symmetrical anatomical region and a second patch corresponding to a second side of the symmetrical anatomical region.

14. The system of claim 13, wherein the first patch is provided to the first set of identical nodes and the second patch is provided to the second set of identical nodes.

15. The system of claim 13, wherein the neural network comprises a third set of identical nodes, wherein the third set of identical nodes is configured to receive a reference patch.

16. The system of claim 12, comprising generating, via the neural network, impact maps configured to identify an influence of one or more voxels.

17. The system of claim 12, wherein the imaging modality is a computerized-tomography (CT) modality.

18. The system of claim 12, comprising:
receiving a plurality of patient images;
determining, via the neural network, a severity of unhealthy tissue in each of the plurality of patient images; and
ranking, by the neural network, each of the plurality of patient images according to the determined severity of unhealthy tissue.

19. The system of claim 12, wherein the defect is at least one of a hemorrhage, an acute infarct, hydrocephalus, a mass effect, and/or a mass lesion.

20. A non-transitory computer-readable medium encoded with computer executable instructions, the computer executable instructions, when executed by a computer in a system for reviewing neural scans, cause the system for reviewing neural scans to execute the steps of:
receiving at least one landmark corresponding to an anatomical region;
receiving a plurality of images of tissue including the anatomical region;
generating a neural network configured to differentiate between healthy tissue and unhealthy tissue within the anatomical region, wherein the neural network is generated by a machine learning process configured to receive the plurality of images of tissue and generate a plurality of weighting factors configured to differentiate between healthy tissue and unhealthy tissue;
receiving at least one patient image of tissue including the anatomical region; and
determining, via the neural network, whether the at least one patient image of tissue includes healthy or unhealthy tissue.

* * * * *